US00PP18605P2

(12) United States Plant Patent
Lloyd

(10) Patent No.: US PP18,605 P2
(45) Date of Patent: Mar. 18, 2008

(54) ***CORDYLINE* PLANT NAMED 'TANA'**

(50) Latin Name: *Cordyline australis×banksii*
Varietal Denomination: TANA

(76) Inventor: Evan David Lloyd, 145a Winchester Street, Ashhurst, Ashhurst 5451 (NZ)

( * ) Notice: Subject to any disclaimer, the term of this patent is extended or adjusted under 35 U.S.C. 154(b) by 113 days.

(21) Appl. No.: 11/436,502

(22) Filed: May 19, 2006

(51) Int. Cl.
*A01H 5/00* (2006.01)

(52) U.S. Cl. ..... Plt./276
(58) Field of Classification Search ..... Plt./276
See application file for complete search history.

(56) References Cited

PUBLICATIONS

UPOV ROM GTITM Computer Database, GTI Jouve Retrieval Software 2007/02 Citation for 'TANA'.*

* cited by examiner

*Primary Examiner*—Wendy Haas

(57) ABSTRACT

A new cultivar of *CORDYLINE* plant named 'TANA' whose leaves are deep purple to black in color with a pronounced glossy upper surface and whose growth habit is strongly clump forming. In combination these characteristics distinguish 'TANA' from all other varieties of *CORDYLINE* known to the inventor.

3 Drawing Sheets

Genus: *CORDYLINE*. Species: *australis×banksii*. Denomination: 'TANA'.

BACKGROUND OF THE INVENTION

The present invention relates to a new and distinct variety of New Zealand Cabbage Tree grown for use as an ornamental for container or the landscape. The new cultivar is known botanically as *CORDYLINE australis×banksii* and will be referred to hereinafter by the cultivar name 'TANA'.

*CORDYLINE australis* is a monocotyledonous tree which is native to New Zealand. It grows to 15 meters in height, at first on a single stem, but dividing into a much-branched crown, each branch forking after producing a flowering stem. The leaves of *CORDYLINE australis* are sword-shaped and predominantly stiffly upright in aspect.

A lesser known species of *CORDYLINE* known as *CORDYLINE banksii,* or New Zealand Forest Cabbage Tree, is also naturalized in New Zealand. At 3 meters to 4 meters in eventual height, *CORDYLINE banksii* is considerably shorter than *CORDYLINE australis,* and the leaves of *CORDYLINE banksii* are lax and drooping.

*CORDYLINES* are widely grown as ornamental plants in New Zealand and in Europe and in the west coast of the United States. Several cultivars are in commerce and are listed as cultivars of *CORDYLINE australis* having been selected as seedlings grown from seed listed as *CORDYLINE australis.* However, the variability in plant habit and leaf characteristics suggests that much of the collected seed has resulted from the cross-pollination of *CORDYLINE australis* and *CORDYLINE banksii,* both of which flower profusely and are capable of cross-pollination.

In 1999, the inventor purchased seed listed and labeled as *CORDYLINE australis purpurea* which the inventor presumed had been collected from one or more dark leafed selections of *CORDYLINE australis.* The inventor sowed the seeds in 1999 in Ashurst, New Zealand. Approximately 300 seeds germinated and were transplanted into pots for further evaluation during 2000. The inventor, who is very familiar with the characteristics of the different species of *CORDYLINE* determined that a number of the seedlings were more typical of the species *CORDYLINE banksii* in as much as these seedlings grew as clumps of lax drooping foliage. The inventor also observed foliage colors ranging from purple to black so that the inventor was able to select one single plant, the subject of the present invention 'TANA' for its unique combination of glossy dark purple to black foliage and a pronounced tendency to form a tight clump. This latter characteristic suggested to the inventor that 'TANA' would be a superior commercial variety by being more prolific in tissue culture multiplication, which is the standard commercial manner of increasing clonal *CORDYLINES.*

The inventor grew 'TANA' for a further six months to the stage at which it was possible for the inventor to split the initial seedling clump into six divisions, and to observe the growth of each division. By 2001 the inventor was able to determine that the characteristics of 'TANA' had remained fixed and stable after the initial asexual propagation by division. Two splits were transferred to a tissue culture laboratory in January 2002 in order to determine whether 'TANA' remained stable and true to type during successive generations of tissue culture propagation. Upon receipt and further growing of the first plants of 'TANA' to be grown by tissue culture, the inventor compared their appearance with the plants which had been propagated only by division, and determined that 'TANA' is stable and reproduces true to type by asexual reproduction by tissue culture, and is a new and distinct cultivar of *CORDYLINE.*

When compared with other varieties of *CORDYLINE* known to the inventor, 'TANA' exhibits broad long lax strap-like leaves which are deep purple to black in color, and which arise from a swollen semi-underground stem. The inventor has also observed that the darkest tones are produced when 'TANA' is grown in full morning sun followed by part shade by mid-day. If grown in full sun throughout, the foliage of 'TANA' tends to be paler.

Although all plants of *CORDYLINE* will eventually produce a lignified stem and will eventually produce flowers, they are sold only at a juvenile stage, namely before any flowering takes place and before whilst the leaves arise from a swollen semi-underground stem. Such juvenile plants are for their attractive foliage which is both architectural and colorful when grown in containers or when incorporated in mixed plantings in containers. 'TANA' has produced no flowers to date.

SUMMARY OF THE INVENTION

The following traits have been repeatedly observed and represent the distinguishing characteristics of the new *CORDYLINE* variety named 'TANA'. In combination these traits set 'TANA' apart from all other varieties of *CORDYLINE* known to the inventor. 'TANA' has not been tested under all possible conditions and phenotypic differences may be observed with variations in environmental, climatic and cultural conditions, however, without any variance in genotype:

1. 'TANA' exhibits broad long lax strap-like leaves.
2. The leaves of 'TANA' range in color from deep purple to black.
3. The upper surface of the leaves of 'TANA' is glossy, appearing to be lacquered.
4. 'TANA' grows as a tight clump and produces numerous basal offsets which may be split away for propagation.

BRIEF DESCRIPTION OF THE DRAWINGS

The accompanying color drawings

Figure 1:
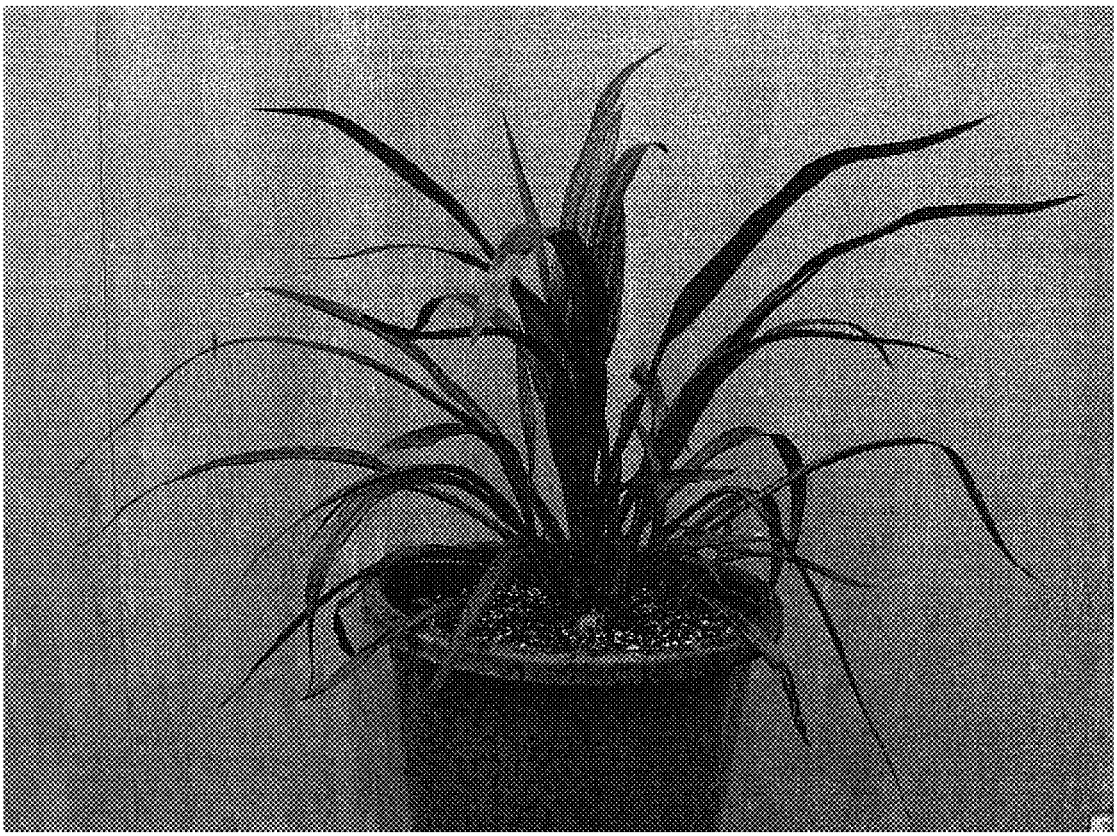
FIGS. 1 to 4 illustrate the overall appearance of 'TANA' showing the colors as true as it is reasonably possible to obtain in colored reproductions of this type. Colors in the drawing may differ from the color values cited in the detailed botanical description, which accurately describe the actual colors of the new variety 'TANA'.

The drawing labeled as FIG. 1 depicts a plant which is 18 months old from a division.

Figure 2:
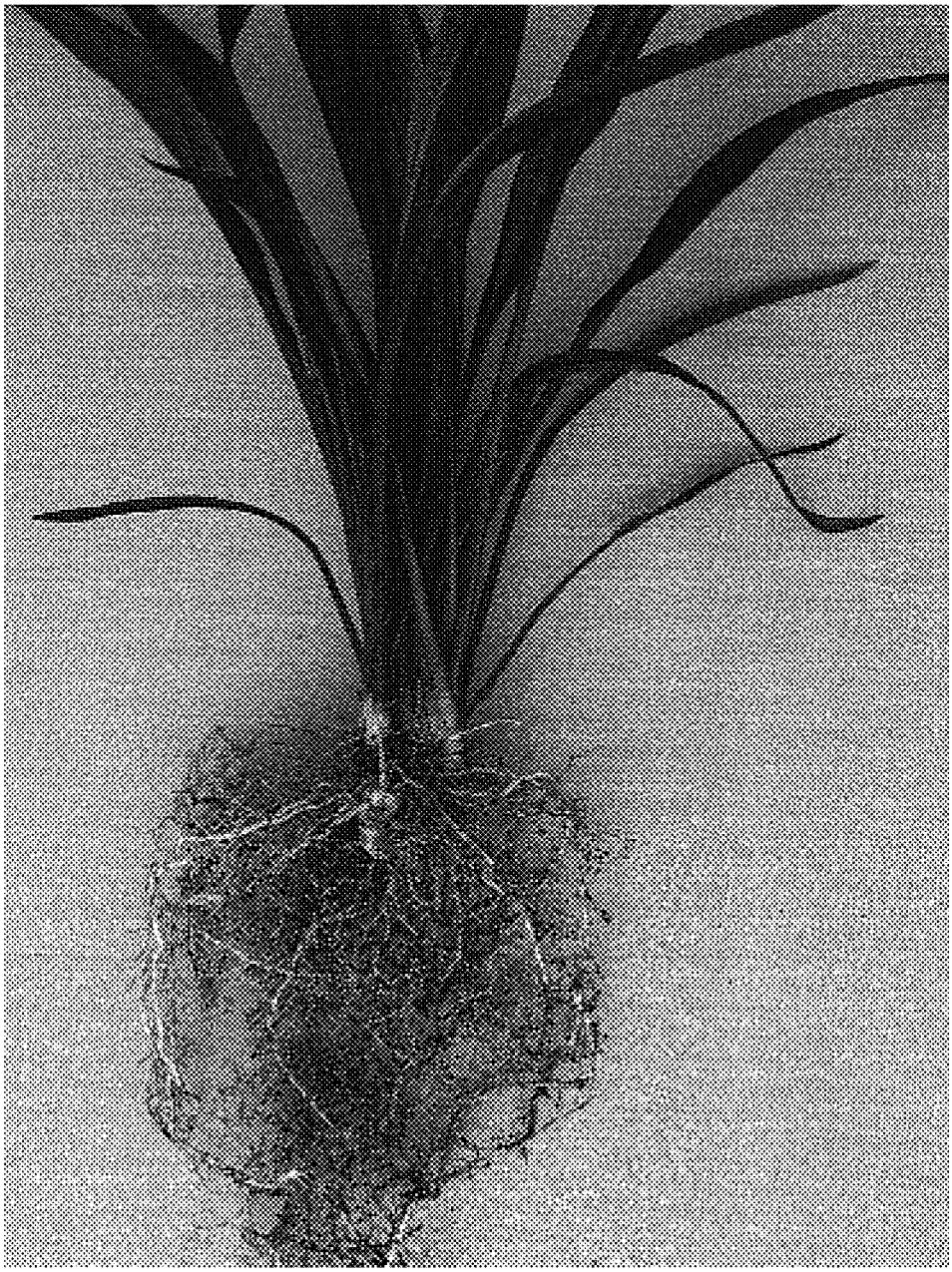

The drawing labeled as FIG. 2 depicts an 18 months old plant which has been root-washed in order to exhibit the swollen semi-underground stem.

Figure 3:
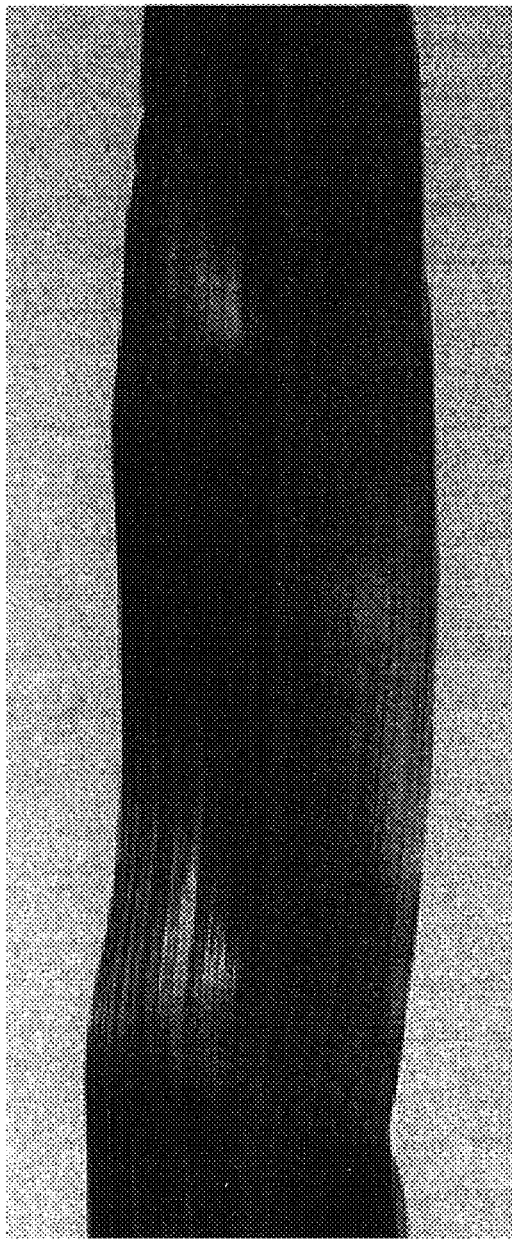

The drawing labeled as FIG. 3 depicts the glossy upper surface of a mature, approximately one year old leaf blade, and exhibits the dark purple to black coloration of the leaf, and slightly lighter colored parallel veins.

Figure 4:
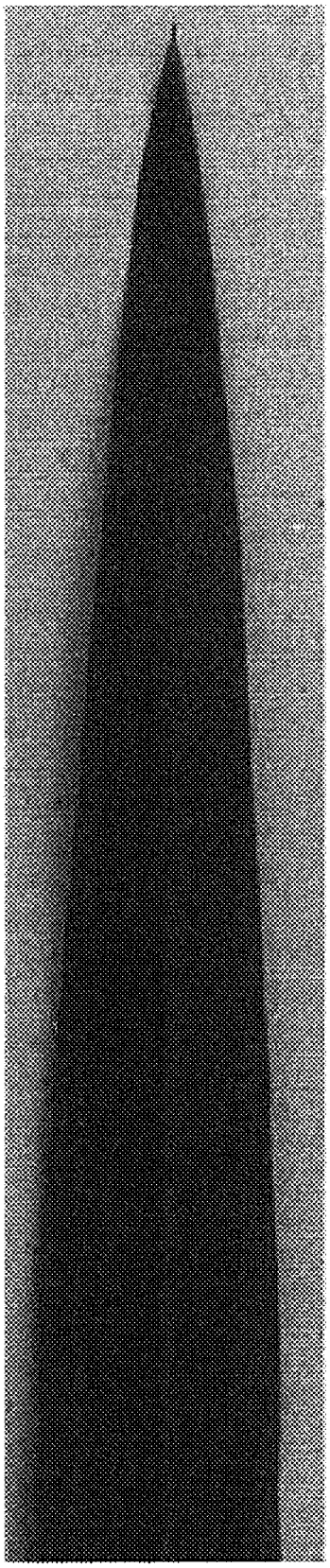

The drawing labeled as FIG. 4 depicts the glaucescent lower surface and the apex of a mature, approximately one year old leaf blade.

All drawings have been made from plants which were approximately 18 months old from a division and which have been grown out-of-doors in a 5 liter container in partial shade in Auckland, New Zealand. No growth regulators have been applied.

BOTANICAL DESCRIPTION OF THE PLANT

The following is a detailed description of the new *CORDYLINE* plant named 'TANA'. Data was collected in Auckland, New Zealand from an 18 month-old plant growing out-of-doors in partial shade in a 5-liter container. The color determinations are in accordance with the 2001 edition of The Royal Horticultural Society Colour Chart, London, England, except where general color terms of ordinary dictionary significance are used. The growing requirements are similar to other *CORDYLINE*.

Botanical classification:
Genus: *CORDYLINE*.
Species: *australis*×*banksii*.
Denomination: 'TANA'.
Common name: New Zealand Cabbage Tree.
Commercial classification: Ornamental annual or as a perennial in USDA hardiness zones 7 or higher.
Plant use: Container or landscape plant.
Cultural requirements: Cultural requirements are well draining soil or growing media, partial shape. Foliage colors enhanced by full morning sun.
Root system: Fibrous.
Plant vigor: Moderate vigor.
Plant growth rate: Slow growing.
Parentage: Seed purchases as *CORDYLINE australis purpurea*.
Plant description:
- *Bloom period.*—'TANA' has produced no flowers to date.
- *Plant habit.*—Lax, weeping, basal branching.
- *Plant dimensions after 18 months.*—Height: 30 cm–40 cm. Width (diameter): 30 cm–40 cm.
- *Plant dimensions after 5 years.*—Height: 70 cm–80 cm. Width (diameter): 70 cm–80 cm.
- *Plant hardiness.*—Plant is hardy to USDA Zone 7.
- *Propagation.*—Propagation is accomplished by division (splits) or by tissue culture.
- *Time to develop roots.*—2 months is needed to develop roots in vitro by the method of tissue culture.
- *Crop time.*—A plant which has been propagated by tissue culture will require approximately 3 months of production in a plug or liner stage in a commercial growing medium before potting into a 2 liter commercial container. In total, the production time from tissue culture to a saleable plant in a 2 liter container is approximately 15 to 18 months.
- *Pest or disease susceptibility and resistance.*—None known to the inventor.

Stem:
- *Stem type.*—Swollen subglobose semi-underground soft caudex.
- *Stem shape.*—Ovate.
- *Stem dimensions.*—Diameter at ground level: 12 mm–15 mm; Length: 15 mm–20 mm.
- *Stem color.*—White below ground eventually becoming 152D where stem gives way to petiole, with intermediate colors close to 199D, 161D.
- *Stem surface.*—Smooth, glossy.

Foliage:
- *Foliage type.*—Evergreen.
- *Quantity of leaves.*—Approximately 20 to 25 at 18 months from a division.
- *Leaf shape.*—Linear.
- *Leaf arrangement.*—Whorled.
- *Leaf apex.*—Acuminate.
- *Leaf base.*—Truncate.
- *Venation pattern.*—Parallel.
- *Vein color* (*adaxial surface*).—183D.
- *Vein color* (*abaxial surface*).—200A, mostly inconspicuous.
- *Leaf margins.*—Entire.
- *Leaf attachment.*—Petiolate.
- *Petiole shape.*—Concave in cross section, sheathing.

*Petiole length.*—8.5 cm.
*Petiole diameter.*—1.7 cm at mid-length.
*Petiole surface.*—Glabrous.
*Petiole color.*—Closest to 152D, sometimes blended with 187B.
*Leaf surface* (*adaxial*).—Glabrous, glossy.
*Leaf surface* (*abaxial*).—Glaucescent.
*Leaf pubescence.*—None observed.
*Leaf width.*—2.8 cm.
*Leaf length.*—44 cm.
*Leaf color.*—Mature leaves, adaxial and abaxial surfaces: 200A lightly blended with 187A.
*Leaf color.*—Juvenile, adaxial surface: 200D lightly blended with N186C.
*Leaf color.*—Juvenile, abaxial surface: Ranges between 200A and 200B, blended with N186C.
*Leaf fragrance.*—No fragrance observed.

Flowers and reproductive organs: No flowers have been produced to date.

It is claimed:

1. A new and distinct cultivar of *CORDYLINE* plant named 'TANA' as described and illustrated herein.

* * * * *